United States Patent [19]
Essen-Moller

[11] Patent Number: 5,507,289
[45] Date of Patent: *Apr. 16, 1996

[54] SYSTEM AND METHOD TO DIAGNOSE BACTERIAL GROWTH

[75] Inventor: Anders Essen-Moller, Stockholm, Sweden

[73] Assignee: Synectics Medical, Inc., Irving, Tex.

[ * ] Notice: The term of this patent shall not extend beyond the expiration date of Pat. No. 5,477,854.

[21] Appl. No.: 216,588

[22] Filed: Mar. 23, 1994

Related U.S. Application Data

[63] Continuation-in-part of Ser. No. 121,468, Sep. 16, 1993.
[51] Int. Cl.[6] .......................................................... A61B 5/00
[52] U.S. Cl. .......................................... 128/635; 128/630
[58] Field of Search ........................... 204/403, 406–408, 204/412, 416; 128/635, 642, 644, 630

[56] References Cited

U.S. PATENT DOCUMENTS

| | | |
|---|---|---|
| 2,162,656 | 6/1939 | Warrington . |
| 2,857,915 | 10/1958 | Sheridan . |
| 3,373,735 | 3/1968 | Gallagher . |
| 3,480,003 | 11/1969 | Crites . |

(List continued on next page.)

FOREIGN PATENT DOCUMENTS

| | | |
|---|---|---|
| 0080680 | 6/1983 | European Pat. Off. . |
| 0241644 | 10/1987 | European Pat. Off. . |
| 2162656 | 6/1973 | Germany . |
| 3140265 | 4/1983 | Germany . |
| 221635 | 5/1985 | Germany . |
| 3523987 | 1/1987 | Germany . |
| 7707275 | 1/1979 | Netherlands . |
| 178028 | 11/1966 | U.S.S.R. . |
| 272477 | 5/1968 | U.S.S.R. . |
| 1502004 | 8/1989 | U.S.S.R. . |

OTHER PUBLICATIONS

"Clinical relevance of ambulatory 24–hour . . . ", Vogten, et al., 1987, pp. 21–31 in Netherlands Journal of Medicine.
"Computerized Axial Manometry of the Esophagus", Bombeck, et al. in Annals of Surgery, vol. 206, No. 4, pp. 465–472, Oct. 1987.
"The laser motility sensor for long–term study of intraesophageal pressure", Schneider et al., in Primary Motility Disorder of the Esophagus, Giuli et al., eds., pp. 64–69 1991.
Assorted promotional material by Synetics Medical, Inc.
Kim et al., American Journal of Clinical Pathology, 1990, vol. 94, pp. 187–191 "The Gastric Juice Urea and Ammonia . . .".
Butcher et al., Digestion, 1992, vol. 53, pp. 142–148, "Use of an Ammonia Electrode for Rapid Quantification of Helicobacter pylori Urease: Its use in the Endoscopy Room and in the . . .".
The New Yorker, Sep. 20, 1993, T. Monmaney, "Marshall's Hunch".
"Oesophageal multipurpose monitoring probe", Baker et al., Anaesthesia, 1983, vol. 38, pp. 892–897.
World Wide Patent Monocrystant . . . (Brochure).
Digestive Diseases, Reprint, vol. 8, Suppl. 1, pp. 60–70, 1990, Scarpignato et al., "Simultaneous Measurement and Recording . . . ".

[ * ] Notice:

*Primary Examiner*—Angela D. Sykes
*Assistant Examiner*—Robert L. Nasser, Jr.
*Attorney, Agent, or Firm*—Stephen C. Glazier

[57] ABSTRACT

A system and a method for monitoring intragastrointestinal concentrations of ammonium, and urease, during short or prolonged periods is presented, as an indicator of the presence and activity of an intragastrointestinal Helicobacter Pylori ("HP") infection, and of other bacterial infections that are similarly located. Ambulatory monitoring is possible. This system and method may be used in the evaluation of treatments for HP and other bacterial infection in the patient. A method is also presented to increase the diagnostic accuracy of the system and method by ingesting urea immediately before or during the monitoring.

30 Claims, 3 Drawing Sheets

U.S. PATENT DOCUMENTS

| | | | |
|---|---|---|---|
| 3,669,095 | 6/1972 | Kobayashi et al. | |
| 3,690,309 | 9/1972 | Pluzhnikov et al. | |
| 3,817,241 | 6/1974 | Grausz. | |
| 3,923,626 | 12/1975 | Niedrach et al. | |
| 4,016,866 | 4/1977 | Lawton. | |
| 4,063,548 | 12/1977 | Klatt et al. | |
| 4,073,287 | 2/1978 | Bradley et al. | |
| 4,119,498 | 10/1978 | Edwall et al. | |
| 4,197,852 | 4/1980 | Schindler et al. | 128/635 |
| 4,208,588 | 6/1980 | Rudin. | |
| 4,214,593 | 7/1980 | Imbruce et al. | |
| 4,265,249 | 5/1981 | Schindler et al. | |
| 4,299,929 | 11/1981 | Sakano et al. | |
| 4,381,011 | 4/1983 | Somers. | |
| 4,442,841 | 4/1984 | Uehara et al. | |
| 4,471,779 | 9/1984 | Antoshkiw et al. | |
| 4,476,871 | 10/1984 | Hon. | |
| 4,478,222 | 10/1984 | Koning et al. | |
| 4,486,290 | 12/1984 | Cahalan et al. | 204/414 |
| 4,487,206 | 12/1984 | Aagard. | |
| 4,503,859 | 3/1985 | Petty et al. | |
| 4,508,103 | 4/1985 | Calisi. | |
| 4,577,640 | 3/1986 | Hofmeister. | |
| 4,593,701 | 6/1986 | Kobayashi et al. | |
| 4,600,015 | 7/1986 | Evans et al. | |
| 4,618,929 | 10/1986 | Miller et al. | |
| 4,631,061 | 12/1986 | Martin. | |
| 4,632,119 | 12/1986 | Reichstein. | |
| 4,642,104 | 2/1987 | Sakamoto et al. | |
| 4,655,225 | 4/1987 | Dahne et al. | |
| 4,681,116 | 7/1987 | Settler. | |
| 4,682,596 | 7/1987 | Bales et al. | |
| 4,691,708 | 9/1987 | Kane. | |
| 4,696,672 | 9/1987 | Mochizuki et al. | |
| 4,700,709 | 10/1987 | Kraig | 128/635 |
| 4,700,799 | 10/1987 | Kawano. | |
| 4,703,757 | 11/1987 | Cohen. | |
| 4,705,503 | 11/1987 | Dorman et al. | |
| 4,729,384 | 3/1988 | Bazenet. | |
| 4,748,113 | 5/1988 | Marshall | 435/12 |
| 4,748,562 | 5/1988 | Miller et al. | |
| 4,757,194 | 7/1988 | Simms. | |
| 4,776,347 | 10/1988 | Matthews. | |
| 4,796,629 | 1/1989 | Grayzel. | |
| 4,803,992 | 2/1989 | Lemelson. | |
| 4,815,471 | 3/1989 | Stobie. | |
| 4,834,101 | 5/1989 | Collison et al. | 128/635 |
| 4,850,371 | 7/1989 | Broadhurst et al. | |
| 4,873,990 | 10/1989 | Holmes et al. | |
| 4,887,610 | 12/1989 | Mittal. | |
| 4,892,101 | 1/1990 | Cheung et al. | |
| 4,901,731 | 2/1990 | Millar. | |
| 4,924,877 | 5/1990 | Brooks. | |
| 4,966,161 | 10/1990 | Wallace et al. | |
| 4,975,581 | 12/1990 | Robinson et al. | |
| 4,976,265 | 12/1990 | Falcial et al. | |
| 4,981,470 | 1/1991 | Bombeck, IV. | |
| 4,986,671 | 1/1991 | Sun et al. | |
| 4,991,590 | 2/1991 | Shi. | |
| 4,996,161 | 2/1991 | Conners et al. | |
| 5,005,584 | 4/1991 | Little. | |
| 5,007,427 | 4/1991 | Suzuki et al. | |
| 5,018,529 | 5/1991 | Tenerz. | |
| 5,022,396 | 6/1991 | Watanabe. | |
| 5,025,786 | 6/1991 | Siegel. | |
| 5,046,497 | 9/1991 | Millar. | |
| 5,047,627 | 9/1991 | Yim et al. | |
| 5,054,487 | 10/1991 | Clarke. | |
| 5,103,835 | 4/1992 | Yamada et al. | |
| 5,105,812 | 4/1992 | Corman. | |
| 5,108,364 | 4/1992 | Takezawa et al. | |
| 5,117,827 | 6/1992 | Stuebe et al. | |
| 5,119,498 | 6/1992 | McNeill et al. | |
| 5,151,598 | 9/1992 | Denen. | |
| 5,158,083 | 10/1992 | Sacristan et al. | 128/635 |
| 5,184,619 | 2/1993 | Austin. | |
| 5,199,443 | 4/1993 | Maurer et al. | |
| 5,207,226 | 5/1993 | Bailin et al. | |
| 5,222,594 | 6/1993 | Sumino. | |
| 5,280,786 | 1/1994 | Wlodarczyk et al. | |
| 5,291,884 | 3/1994 | Heinemann et al. | |
| 5,301,673 | 4/1994 | Rabito et al. | |
| 5,314,804 | 5/1994 | Bogulaski et al. | 435/12 |

OTHER PUBLICATIONS

Hojgaard et al., "A New Method for Measurement of the Electrical Potential Difference Across the Stomach Wall", 1991. pp. 847–858.

"Ambulatory Monitoring of Gastric Emptying", Hoeft et al., May 16, 1993, American Assoc. of the Study of Live Diseases.

SYSTEM AND METHOD TO DIAGNOSE BACTERIAL GROWTH

This application is a continuation-in-part of prior co-pending application Ser. No. 08/121,468, filed 16 Sep. 1993.

FIELD OF INVENTION

The present invention involves a system and a method for the continuous measurement, on a stationary or ambulatory basis, of various internal factors of a human patient. Specifically the invention monitors the concentration of ammonium and of urease in the gastro-intestinal tract of the patient. More specifically, this data is used as an indicator of the presence of bacteria and especially of Helicobacter Pylori ("HP") infection in the stomach or gastro-intestinal tract, as well as of the effectiveness of treatment for a bacterial infection, and especially an HP infection in the stomach or gastro-intestinal tract. The system may also be used for in vivo monitoring of ammonium producing bacteria in the colon and other parts of the gastro-intestinal tract. A method is also shown to increase the accuracy of the present invention by ingestion of urea by the patient prior to use.

BACKGROUND

HP is a recently discovered bacteria increasingly being recognized as an etiologic agent for a variety of upper gastrointestinal diseases (see Kim et al., in the *American Journal of Clinical Pathology*, 1990, volume 94, pages 187 through 191) including gastritis, ulcers, cancer, and associated disorders. In the case of a stomach infection, HP may be identified in the mucus layer adjacent to columnar epithelial cells. In the case of a stomach infection, HP produces a urease enzyme and influences the ammonium levels in the gastro-intestinal tract of the patient.

It has recently been discovered that an ammonium electrode can be used to indicate the presence of HP bacteria in gastric tissue. (See Butcher, et al., in *Digestion*, 1992, volume 53, pages 142 through 148). However, this discovery was of the use of such an electrode on in vitro (cell cultures in a laboratory) and not in vivo (in a living patient). Biopsies were required, and information was obtained only for the condition present at the time that the biopsy was obtained. No in patient, continuous, real time, ambulatory monitoring was indicated, nor was the possibility of combining such measurements, with simultaneous measurement of other related parameters.

Diagnosis and monitoring of an HP infection can be made in a variety of ways including aspiration, a test for antibodies (serology), and a test of the expiratory gas (mass spectrometry), of the patient. Presently treatment for HP infections often involves use of a combination of drugs including antibiotics and components that directly increase the pH of the gastric juice.

To diagnose and monitor the results of treatment for HP infection, serological methods are now often used. Several ELISA tests are commercially available. However, serological methods may not be optimal, since antibodies may remain the blood for months after an infection is eliminated. Likewise, mass spectrometry of expiration gases may be unsatisfactory because the procedure can be cumbersome to perform and may give false results due to momentary fluctuations in the makeup of such gases. Histology can be a reliable way to detect the presence of HP, but requires a biopsy.

However, the inventor of the present invention has found that, by in vivo intragastro-intestinal monitoring of ammonium levels over a prolonged time period such as an hour or more, the activity of the HP bacteria may be monitored and diagnosed, as well as the results of any treatment thereby immediately and accurately accessed.

It is an object of the present invention to realize a simple system and method, suitable for ambulatory use, that measure intragastrointestinal ammonium concentrations with an intragastrointestinal catheter, over a prolonged period. It is a further object of the present invention to present variations of ammonium concentrations during the various periods of a circadian cycle, such as after meals, during sleep, and so forth. This permits diagnosis and evaluation of treatments for HP infections. Furthermore the invention may be used to simultaneously measure other intragastrointestinal parameters such as potential difference, pH, and motility parameters.

Characteristic of HP is its abundant production of urease. This fact is used in the diagnostic CLO test where a biopsy is put into contact with a urea marked glass plate. Because urease splits urea into carbon dioxide and ammonia with a consequent increase of pH, a pH dependent change in color (to phenol-red) is indicative of the presence of HP. Again, this method has the drawback of an obligatory biopsy.

A non-invasive breath test, presently under development, uses the carbon isotope 13C to mark urea. The marked urea is then administered in liquid form to the patient. If urease is present, then the marked carbon is split off the urea, absorbed into the patient's blood circulation, and finally exhaled as carbon dioxide. The exhaled carbon dioxide can be detected with a mass spectrometer. This is a somewhat cumbersome method as it requires specially marked carbon and an expensive mass spectrometer.

SUMMARY OF THE INVENTION

The present invention is a system and a method for in vivo monitoring intragastrointestinal concentrations of ammonium during prolonged periods, as an indicator of the presence and activity of an intragastrointestinal Helicobacter Pylori ("HP") and other ammonium producing infections. Ambulatory monitoring is possible with the invention. This system and method may be used in the evaluation of treatments for HP infection in the patient.

In the present invention, an ambulatory digital recorder, is connected to an ammonium sensitive intragastrointestinal catheter and a reference Ag/AgCl catheter.

The recorder is calibrated by the method of the invention.

After this calibration, the ammonium catheter is put into its intragastrointestinal position and the recorder samples, once per second, the values of ammonium concentration continuously measured by the ammonium catheter. After recording, the stored values are uploaded to a computer which analyzes the ammonium data.

During the recording period, the patient can be exposed to various forms of treatment, including the administration of various types of meals, antibiotics, pH increasing agents, potential difference influencing agents, prokinetic motility agents, and others, in order to find the best way of reaching and eliminating the HP bacteria.

In a variation of the present invention, urea is ingested by the patient immediately before or during monitoring. If HP infection is present, then HP produces urease, and the urease reacts with urea to make ammonia. Hence, in the presence of HP infection, adding urea increases the ammonia level, which increases the diagnostic accuracy of the method of the invention and its apparatus. This variation of the invention adds diagnostic accuracy that results from measuring the gastro-intestinal concentration of ammonia after ingestion of urea. The measurement of ammonium concentration may be made on one or a few occasions before and after ingestion of urea. The measurement may also be done over a prolonged period of time during which the patient may return to his home with an ambulatory recorder. This permits a 24 hour study, during which the patient may ingest several doses of known amounts of urea. The recorder may also measure other parameters such a pH and potential difference.

The present invention is different from the CLO test in that the present invention does not require a biopsy, does not require an external plate covered with urea, and does not measure the change in ammonium concentration. Similarly, the present invention is different from the breath test under development because the present invention does not need radio-marked urea, does not measure concentrations of radio-marked carbon dioxide, does not use exhaled gas for measurement, and does not require a mass spectrometer.

DETAILED DESCRIPTION OF THE PREFERRED EMBODIMENT

Figure 1:
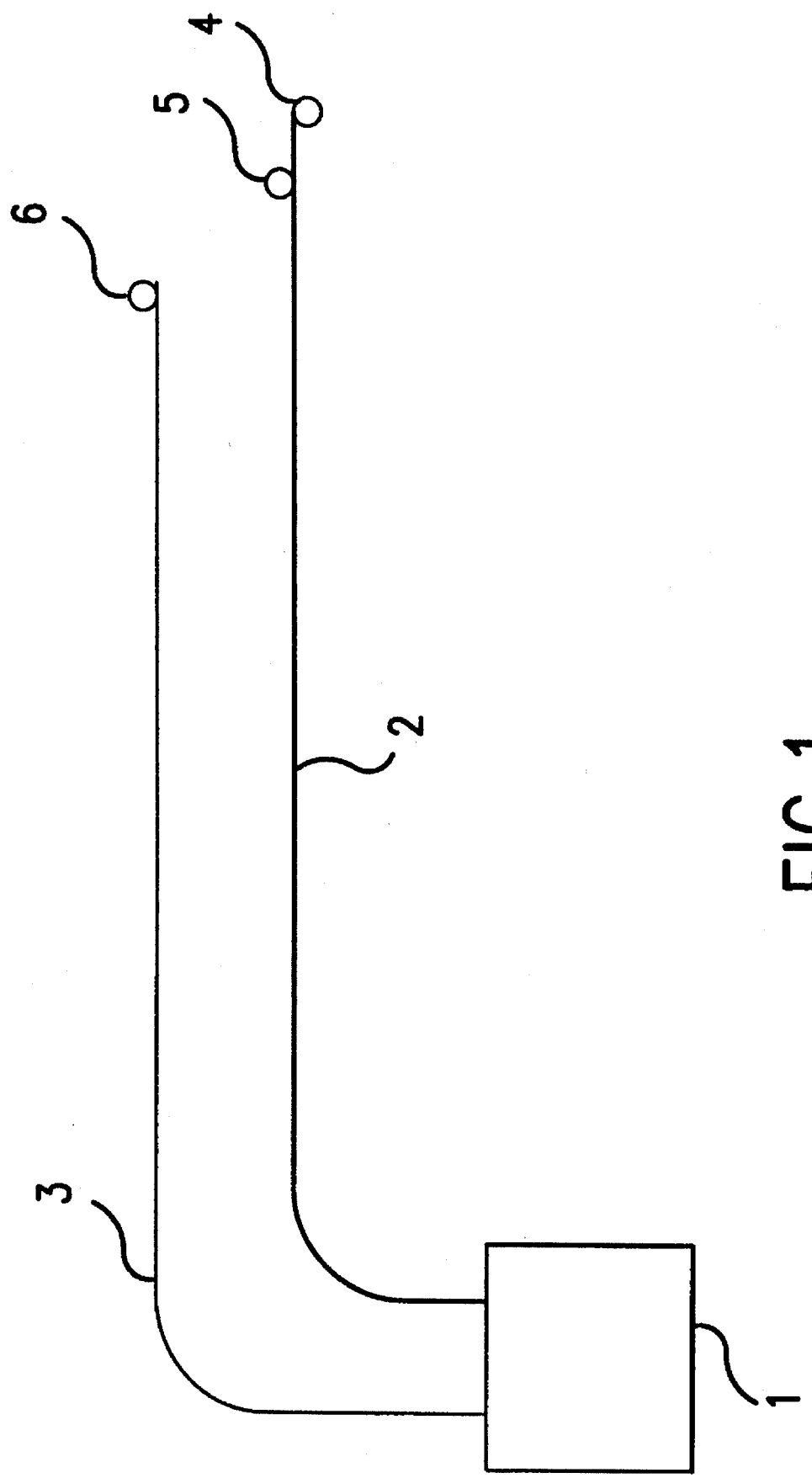
FIG. 1 shows a schematic view of the ambulatory system for monitoring intragastrointestinal ammonium concentrations.

In FIG. 1, a known ambulatory digital recorder 1, such as a Microdigitrapper described in European Patent Specification #0,356,603, is connected to an ammonium sensitive glass intragastrointestinal electrode 4 and a reference Ag/AgCl electrode 6. The ammonium electrode 4 is attached near the distal end of an intragastrointestinal catheter 2, and such electrode 4 communicates to the recorder 1 through the catheter 2 when the catheter 2 is attached to the recorder 1. The Ag/AgCl electrode 6 is attached near the distal end of a catheter 3, and such electrode 6 communicates to the recorder 1 through the catheter 3 when the catheter 3 is attached to the recorder 1. The catheters are made of PVC medical tubing of dimensions commonly used for medical catheters, and the electrodes 4 and 6 communicate through a wire running inside their respective catheters 2 and 3 to the recorder 1.

The recorder 1 is calibrated in reference solutions with ammonium concentrations of $10^{-2}$ M and $10^{-4}$ M NH Cl. This calibration is done while both electrodes 4 and 6 are connected to the recorder 1. First the reference electrode 6 is applied to the skin of the patient. Then the patient's finger and the ammonium electrode 4 are both inserted in turn to each of the two NHCl reference solutions.

After this calibration, the ammonium electrode 4 and its catheter 2 is put into its intragastrointestinal position and the recorder 1 samples, once per second, the values of ammonium concentration continuously measured by the ammonium sensitive electrode 4. Measured values are stored in a RAM memory in the recorder of adequate memory size to store all the values sampled over a period of several days. After;recording, the stored values are uploaded to a computer which analyses the ammonium data, or to a printer for graphic representation or printing.

A level of ammonium concentration above normal for a significant period would be correlated to an HP infection and would indicate a diagnosis of the same, whereas a concentration always at a normal level would correlate with no such infection and would indicate no such diagnosis. This correlation can be done by the computer analyzing the data, or manually after the data is printed out.

During the recording period, the patient can be exposed to various forms of treatment, including administration of antibiotics, pH increasing agents, potential difference influencing agents, prokinetic motility agents, and others, in order to find the best way of reaching and eliminating the HP bacteria.

Falling ammonium concentration levels during the monitoring period would be correlated to reduced HP activity, and would indicate that the treatment of the infection was being successful. No such fall in concentration, or only a temporary fall, would be correlated to sustained HP activity and would indicate that the treatment of the infection was failing, or would correlate to the conclusion that no infection was present.

In the embodiment of the present invention using the ingestion of urea, a certain amount of urea crystals are dissolved in water and administered orally to the patient. If HP activity is present, then urease is also present. The urease splits off ammonium from the ingested urea, and the ammonium is then registered in the recorder's memory RAM and displayed on the recorder's display. By comparing the ammonium concentration before and after the ingestion of urea, further information about any HP activity is developed. If there is an HP infection, then the ammonia level will go up after urea is ingested. If there is no HP infection, then the ammonia level will have little or no change when the urea is added. In addition, simultaneous recording of shifts in gastro-intestinal pH provide further enhancements to the diagnostic accuracy of the present invention, since the additional ammonia produced by the urease reacting with the urea causes an increase in gastro-intestinal pH. If an HP infection exists, then the pH will also increase when the urea is ingested, together with the increase in ammonia. If there is no HP infection, then the pH will show little or no change when the urea is ingested, just as the ammonia level will show little or no change. The patient may be tested once in the doctor's office, or alternatively the patient may be given several doses of urea which the patient may ingest over a prolonged period of time with ambulatory monitoring, for example in the patient's home.

For convenience of discussion, HP infection is often specifically discussed in this specification. However the present invention can be used regarding any gastro-intestinal infection of bacteria than produces urease or ammonia or changes in pH or any of the other parameters that can be measured by the present invention. The readings for the parameters that are obtained are correlated with the expected readings for the same parameters for the bacteria being investigated, and if the correlation is positive then the target bacteria is concluded to have been found. Changes over time of the correlation from positive to negative would indicate that the bacteria has been successfully treated in that period. The present invention can also be used to detect the presence of urease in the gastro-intestinal tract by the measurement of intragastro-intestinal ammonia levels, either with or without the ingestion of urea, and this can be taken as an indicator of the present of any target source of urease production, or merely of urease presence per se. The efforts can be done in conjunction with the measurement of intra-gastro-intestinal pH, which is also an indicator of ammonia, together with the direct sensing of ammonia, as indicators of urease and producers of urease.

Also, the measurement and correlation methods described herein can either be done in short monitoring sessions, or in longer time periods of 24 hours or more.

Also the response over time of urease, ammonia, and/or pH levels, during which urea is or is not ingested, or during which various treatments of bacterial infections are given, can be used to increase the accuracy of these methods, and to evaluate the effectiveness of the treatments, respectively.

These methods of the present invention permit the use of urea that is not radio-marked.

The embodiments illustrated and discussed in this specification are intended only to teach those skilled in the art the best way known by the inventor to make and use the invention. Nothing in the specification should be considered as limiting the scope of the present invention. Changes could be made by those skilled in the art to produce equivalent systems without departing from the invention. The present invention should only be limited by the following claims and their legal equivalents.

Figure 3:
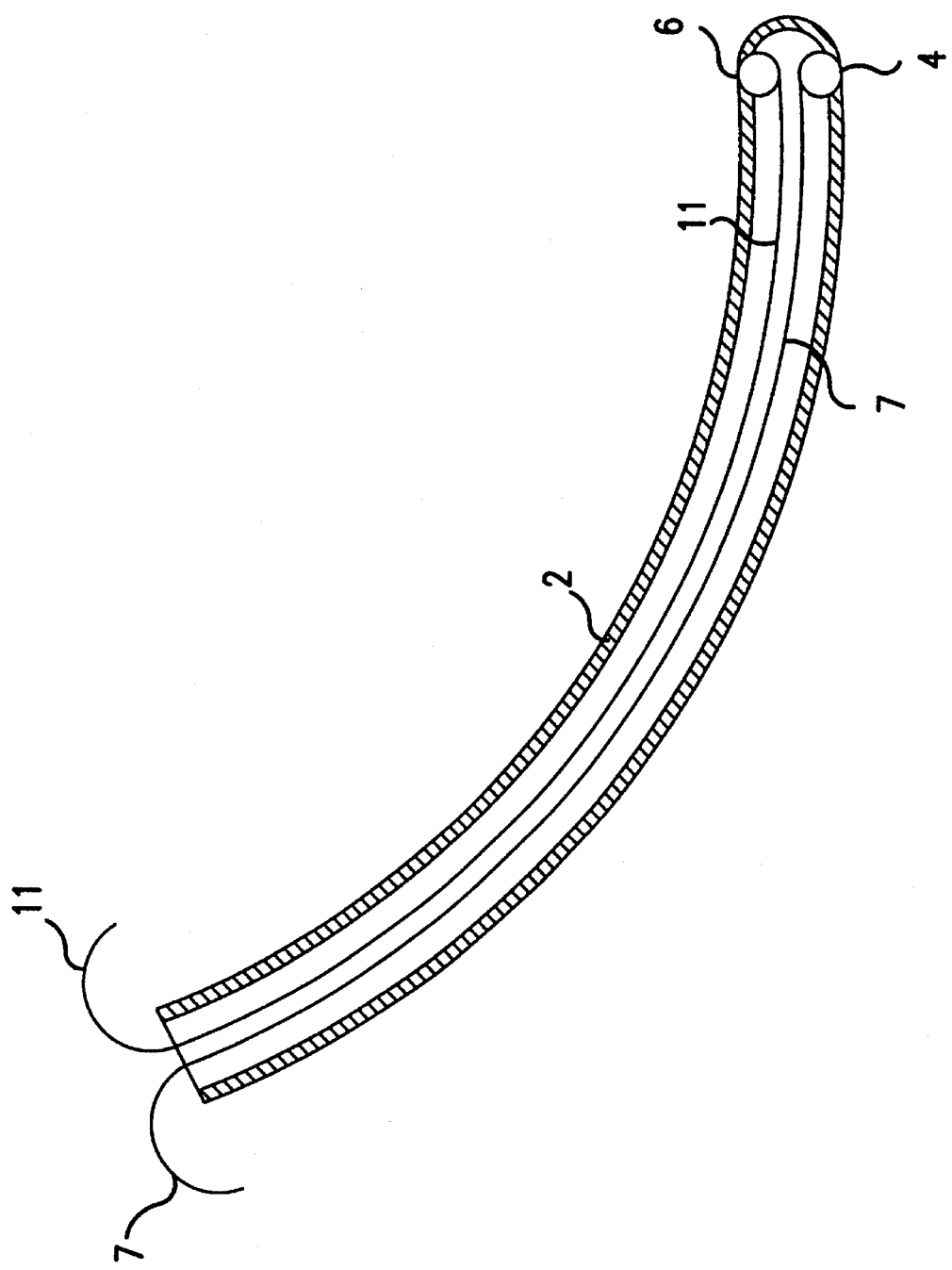
FIG. 3 shows a cross-sectional view of another intragastrointestinal catheter of the system.

Furthermore, the catheter 2 can also contain another sensor 5 near its distal end, also communicating through the catheter 2 to the recorder 1. This would permit the recorder to sample and record readings of some other parameter in the gastrointestinal area, simultaneously with ammonium. The other sensor 5 may be, for example, a pH sensor, a potential difference sensor, a pressure sensor, or a motility sensor. Also, reference electrode 6 may be built into catheter 2, as shown in FIG. 3, where reference electrode 6 communicates to the proximal end of the catheter 2 through wire 11.

Figure 2:
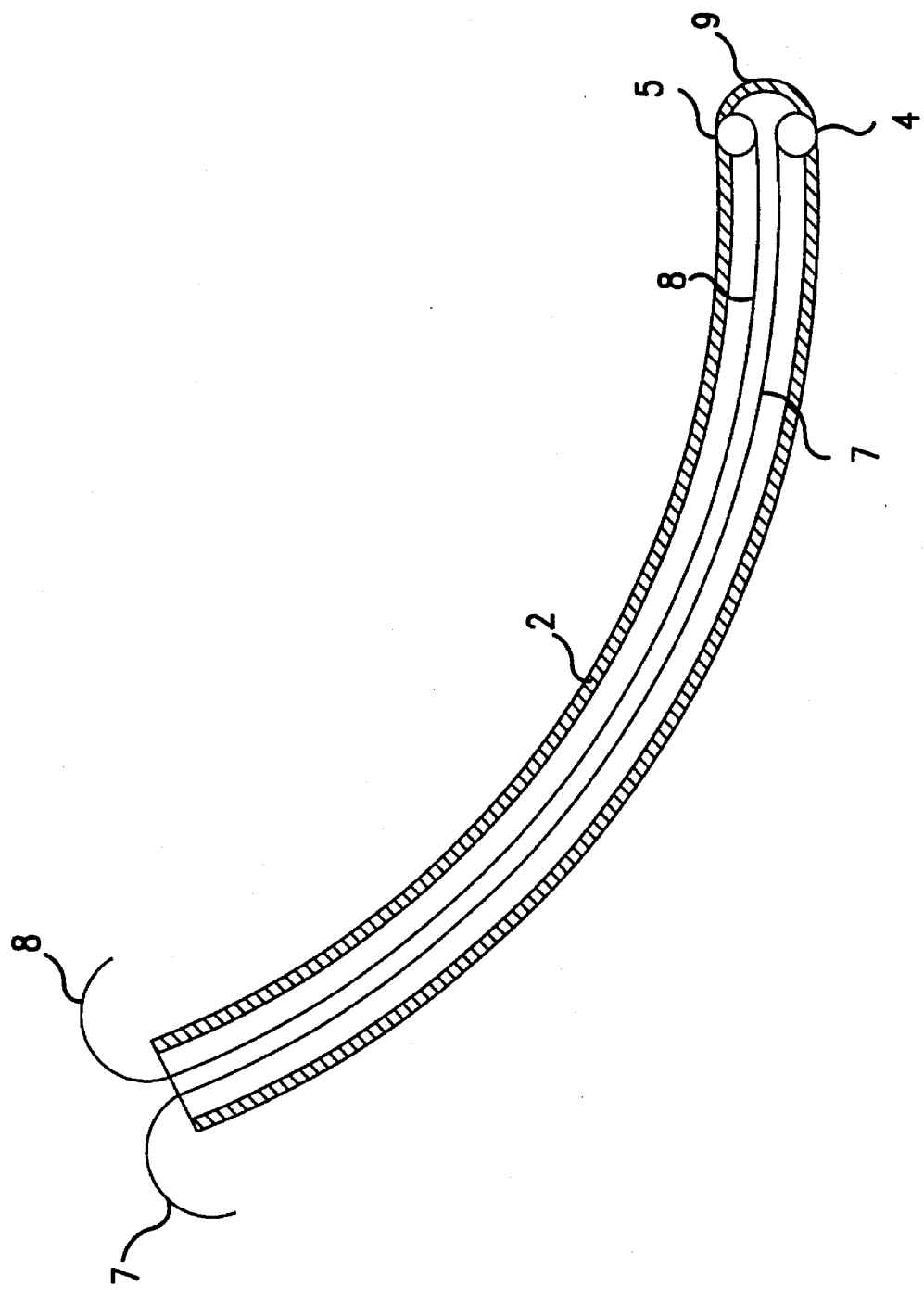
FIG. 2 shows a cross-sectional view of a intragastrointestinal catheter of the system.

FIG. 2 shows the catheter body 2, the ammonium electrode 4, the wire 7 by which the electrode 4 communicates to the proximal end of the catheter 2, the other sensor 5, and the wire 8 by which the sensor 5 communicates to the proximal end of the catheter 2. Some types of sensor 5 will not use a wire 8, but will communicate to the proximal end of the catheter 2 pneumatically or hydraulically through the interior cavity 9 of the catheter 2.

I claim:

1. A system for monitoring a gastrointestinal presence of at least one of an urease producing bacterial strain and an ammonium producing bacterial strain comprising:
   (a) an electronic recorder,
   (b) a first catheter with a first sensor for detecting the gastrointestinal presence of the bacterial strain, the first sensor being a gastrointestinal ammonium sensing electrode, the first catheter being interconnected with the recorder, and the gastrointestinal ammonium sensing electrode communicating through the first catheter to the recorder, and
   (c) a second catheter with a reference Ag/AgCl electrode near a distal end of said second catheter, the second catheter being interconnected with the recorder, and the reference Ag/AgCl electrode communicating, through the second catheter, with the recorder said recorder communicating with said sensor and said electrode to determine the gastrointestinal presence of said bacterial strain.

2. The invention in claim 1, wherein the electronic recorder is an ambulatory digital electronic recorder with RAM memory.

3. The invention in claim 1, wherein the gastrointestinal ammonium Sensing electrode is an ammonium sensitive glass gastrointestinal electrode.

4. The invention in claim 1, and further comprising a second sensor communicating through the first catheter with the recorder, said second sensor being selected from the group consisting of a pH sensor, a potential difference sensor, a pressure sensor, and a motility sensor and sensing a parameter other than gastrointestinal ammonium.

5. A system for monitoring a gastrointestinal presence of at least one of an urease producing bacterial strain and an ammonium producing bacterial strain comprising:
   (a) an electronic recorder, comprising an ambulatory digital electronic recorder with RAM memory,
   (b) a first catheter with a first sensor for detecting the gastrointestinal presence of the bacterial strain, the first sensor being a gastrointestinal ammonium sensing electrode, the first catheter being interconnected with the recorder, and the gastrointestinal ammonium sensing electrode communicating through the first catheter with the recorder, the gastrointestinal ammonium sensing electrode further comprising an ammonium sensitive glass gastrointestinal electrode,
   (c) a second catheter with a reference Ag/AgCl electrode near a distal end of said second catheter, the second catheter being interconnected with the recorder, and the reference Ag/AgCl electrode communicating, through the second catheter, with the recorder, and
   (d) a second sensor communicating through the first catheter with the recorder, said second sensor being selected from the group consisting of a pH sensor, a potential difference sensor, a pressure sensor, and a motility sensor and sensing a parameter other than gastrointestinal ammonium said recorder communicating with said first sensor, said second sensor, and said electrode to determine the gastrointestinal presence of said bacterial strain.

6. A system for monitoring a gastrointestinal presence of at least one of an urease producing bacterial strain and an ammonium producing bacterial strain comprising:
   (a) an electronic recorder, and
   (b) a catheter interconnected with the recorder, the catheter having (i) a first sensor for detecting the gastrointestinal presence of the bacterial strain, the first sensor being a gastrointestinal ammonium sensing electrode communicating, through the catheter, with the recorder, and (ii) a second sensor, the second sensor being a reference Ag/AgCl electrode communicating, through the catheter, with the recorder said recorder communicating with said first sensor and said second sensor to determine the gastrointestinal presence of said bacterial strain.

7. The invention in claim 6, wherein the electronic recorder is an ambulatory digital electronic recorder with RAM memory.

8. The invention in claim 6, wherein the gastrointestinal ammonium sensing electrode is an ammonium sensitive glass gastrointestinal electrode.

9. The invention in claim 6, and further comprising a third sensor communicating through the catheter with the recorder, said third sensor being selected from the group consisting of a pH sensor, a potential difference sensor, a pressure sensor, and a motility sensor and sensing a parameter other than gastrointestinal ammonium.

10. A system for monitoring a gastrointestinal presence of at least one of an urease producing bacterial strain and an ammonium producing bacterial strain comprising:

(a) an electronic recorder, comprising an ambulatory digital electronic recorder with RAM memory, (b) a catheter interconnected with the recorder, the catheter having (i) a first sensor for detecting the gastrointestinal presence of the bacterial strain, the first sensor being a gastrointestinal ammonium sensing electrode communicating, through the catheter, with the recorder, and (ii) a second sensor, the second sensor being a reference Ag/AgCl electrode communicating, through the catheter, with the recorder, and (c) a third sensor communicating through the catheter with the recorder, said third sensor being selected from the group consisting of a pH sensor, a potential difference sensor, a pressure sensor, and a motility sensor and sensing a parameter other than gastrointestinal ammonium said recorder communicating with said first sensor, said second sensor, and said third sensor to determine the gastrointestinal presence of said bacterial strain.

11. A method for diagnosing a presence of one of an urease producing bacterial strain and an ammonium producing bacterial strain infection in a patient, determining an effectiveness of a treatment for the infection and monitoring gastrointestinal ammonium levels, comprising the steps of:

(a) attaching an ammonium sensing catheter and a reference Ag/AgCl catheter to an electronic recorder, (b) calibrating the ammonium sensing catheter with the reference Ag/AgCl catheter, (c) inserting the ammonium sensing catheter into a gastrointestinal position in the patient, (d) recording, in RAM memory in the electronic recorder, periodically, during a monitoring period, a plurality of ammonium concentration readings from the ammonium sensing catheter, (e) uploading recorded ammonium concentration readings to one of an electronic computer and a printer, (f) presenting graphically the recorded ammonium concentration readings, (g) diagnosing the presence of the infection from said recorded ammonium concentration readings, and (h) determining the effectiveness of the treatment from said recorded concentration readings.

12. The invention in claim 11, and further comprising the step of:

correlating the ammonium concentration readings with expected ammonium concentration readings of a particular infection.

13. The invention in claim 11, and further comprising the steps of:

(a) exposing the patient to a treatment for the infection while recording the ammonium concentration readings, and (b) correlating the recorded ammonium concentration readings with expected ammonium concentration readings of an effective treatment of the infection.

14. A method for diagnosing a presence of a Helicobacter Pylori infection in a patient, determining an effectiveness of a treatment for the infection and monitoring gastrointestinal ammonium levels, comprising the steps of:

(a) attaching an ammonium sensing catheter and a reference Ag/AgCl catheter to an electronic recorder, (b) calibrating the ammonium sensing catheter with the reference Ag/AgCl catheter, (c) inserting the ammonium sensing catheter into a gastrointestinal position in the patient, (d) recording, in RAM memory in the electronic recorder, periodically, during a monitoring period, a plurality of ammonium concentration readings from the ammonium sensing catheter, (e) uploading recorded ammonium concentration readings to an electronic computer, (f) correlating the ammonium concentration readings with expected ammonium concentration readings of the Helicobacter Pylori infection to obtain a correlation, (g) diagnosing the presence of the Helicobacter Pylori infection based on whether the correlation is positive or negative, and (h) determining the effectiveness of the treatment from said recorded concentration readings.

15. The invention in claim 14, and further comprising the step of:

presenting graphically the recorded ammonium concentration readings and the correlation.

16. The invention in claim 14, and further comprising the steps of:

(a) attaching a pH sensing catheter to the electronic recorder, (b) inserting the pH sensing catheter into a gastrointestinal position in the patient, (c) recording, in RAM memory in the electronic recorder, periodically, during a monitoring period, a plurality of pH readings from the pH sensing catheter, (d) uploading, recorded pH readings to the electronic computer, (e) correlating the pH readings with the ammonium concentration readings and with expected pH readings and ammonium concentration readings of the Helicobacter pylori infection to obtain a correlation, and (f) indicating whether the correlation is positive or negative.

17. A method for diagnosing a presence of a Helicobacter Pylori infection in a patient, determining an effectiveness of a treatment for the infection and monitoring gastrointestinal ammonium levels, comprising the steps of:

(a) attaching an ammonium sensing catheter and a reference Ag/AgCl catheter to an electronic recorder, (b) calibrating the ammonium sensing catheter with the reference Ag/AgCl catheter, (c) inserting the ammonium sensing catheter into a gastrointestinal position in the patient, (d) ingesting urea into the patient, (e) recording, in RAM memory in the electronic recorder, periodically, during a monitoring period, a plurality of ammonium concentration readings from the ammonium sensing catheter, (f) uploading recorded ammonium concentration readings to an electronic computer, (g) correlating the ammonium concentration readings with expected ammonium concentration readings of the Helicobacter Pylori infection to obtain a correlation, (h) diagnosing the presence of the Helicobacter Pylori infection based on whether the correlation is positive or negative, and (i) determining the effectiveness of the treatment from said recorded concentration readings.

18. The invention in claim 17, and further comprising the step of:

presenting graphically the recorded ammonium concentration readings and the correlation.

19. The invention in claim 17, and further comprising the steps of:

(a) attaching a pH sensing catheter to the electronic recorder, (b) inserting the pH sensing catheter into a gastrointestinal position in the patient, (c) recording, in RAM memory in the electronic recorder, periodically, during a monitoring period, a plurality of pH readings from the pH sensing catheter, (d) uploading recorded pH readings to the electronic computer, (e) correlating the pH readings with the ammonium concentration readings and with expected pH readings and ammonium concentration readings of the Helicobacter Pylori infection to obtain a correlation, and (f) indicating whether the correlation is positive or negative.

20. A system for monitoring a gastrointestinal presence of at least one of an urease producing bacterial strain and an ammonium producing bacterial strain comprising:

(a) an electronic recorder, and (b) a catheter with a gastrointestinal ammonium sensing electrode for detecting the gastrointestinal presence of the bacterial strain, the catheter attached to the recorder, and the gastrointestinal ammonium sensing electrode communicating through the catheter to the attached recorder said recorder communicating with said electrode to determine the gastrointestinal presence of said bacterial strain.

21. The system defined by claim 20, wherein the electronic recorder is an ambulatory digital electronic recorder with RAM memory.

22. The system defined by claim 20, wherein the gastrointestinal ammonium sensing electrode is an ammonium sensitive glass gastrointestinal electrode.

23. The system defined by claim 20, and further comprising a second sensor communicating through the catheter with the recorder, said second sensor being selected from the group consisting of a pH sensor, a potential difference sensor, a pressure sensor, and a motility sensor and sensing a parameter other than gastrointestinal ammonium.

24. A system for monitoring a gastrointestinal presence of at least one of an urease producing bacterial strain and an ammonium producing bacterial strain comprising:

(a) an electronic recorder, comprising an ambulatory digital electronic recorder with RAM memory, (b) a catheter with (i) a gastrointestinal ammonium sensing electrode for detecting the gastrointestinal presence of the bacterial strain, the catheter attached to the recorder, and the gastrointestinal ammonium sensing electrode communicating through the catheter to the recorder, the gastrointestinal ammonium sensing electrode further comprising an ammonium sensitive glass gastrointestinal electrode, and (ii) a second sensor, the second sensor communicating through the catheter to the recorder, the second sensor being one member selected from the group consisting of a pH sensor, a potential difference sensor, a pressure sensor, and a motility sensor and sensing a parameter other than gastrointestinal ammonium said recorder communicating with said electrode and said second sensor to determine the gastrointestinal presence of said bacterial strain.

25. A method for diagnosing a presence of a Helicobacter Pylori infection in a patient, determining an effectiveness of a treatment for the infection and monitoring gastrointestinal ammonium levels, comprising the steps of:

(a) attaching an ammonium sensing catheter to an electronic recorder, (b) inserting the ammonium sensing catheter into a gastrointestinal position in the patient, (c) recording, in RAM memory in the electronic recorder, periodically, during a monitoring period, a plurality of ammonium concentration readings from the ammonium sensing catheter, (d) uploading recorded ammonium concentration readings to an electronic computer, (e) correlating the ammonium concentration readings with expected ammonium concentration readings of the Helicobacter Pylori infection to obtain a correlation, (f) diagnosing the presence of the Helicobacter Pylori infection based on whether the correlation is positive or negative, and (g) determining the effectiveness of the treatment from said recorded concentration readings.

26. The invention in claim 25, and further comprising the step of:

presenting graphically the recorded ammonium concentration readings and the correlation.

27. The invention in claim 25, and further comprising the steps of:

(a) attaching a pH sensing catheter to the electronic recorder, (b) inserting the pH sensing catheter into a gastrointestinal position in the patient, (c) recording, in RAM memory in the electronic recorder, periodically, during a monitoring period, a plurality of pH readings from the pH sensing catheter, (d) uploading recorded pH readings to the electronic computer, (e) correlating the pH readings with the ammonium concentration readings and with expected pH readings and ammonium concentration readings of the Helicobacter Pylori infection to obtain a correlation, and (f) indicating whether the correlation is positive or negative.

28. A method for diagnosing a presence of a Helicobacter Pylori infection in a patient, determining an effectiveness of a treatment for the infection and monitoring gastrointestinal ammonium levels, comprising the steps of:

(a) attaching an ammonium sensing catheter to an electronic recorder, (b) inserting the ammonium sensing catheter into a gastrointestinal position in the patient, (c) ingesting urea into the patient, (d) recording, in RAM memory in the electronic recorder, periodically, during a monitoring period, a plurality of ammonium concentration readings from the ammonium sensing catheter, (e) uploading recorded ammonium concentration readings to an electronic computer, (f) correlating the ammonium concentration readings with expected ammonium concentration readings of the Helicobacter Pylori infection to obtain a correlation, (g) diagnosing the presence of the Helicobacter Pylori infection based on whether the correlation is positive or negative, and (h) determining the effectiveness of the treatment from said recorded concentration readings.

29. The invention in claim 28, and further comprising the step of:

presenting graphically the recorded ammonium concentration readings and the correlation.

30. The invention in claim 28, and further comprising the steps of:

(a) attaching a pH sensing catheter to the electronic recorder, (b) inserting the pH sensing catheter into a gastrointestinal position in the patient, (c) recording, in RAM memory in the electronic recorder, periodically, during a monitoring period, a plurality of pH readings from the pH sensing catheter, (d) uploading recorded pH readings to the electronic computer, (e) correlating the pH readings with the ammonium concentration readings and with expected pH readings and ammonium concentration readings of the Helicobacter Pylori infection to obtain a correlation, and (f) indicating whether the correlation is positive or negative.

* * * * *